US012728188B2

(12) United States Patent
Wolf et al.

(10) Patent No.: US 12,728,188 B2
(45) Date of Patent: Sep. 8, 2026

(54) DEVICE AND METHOD FOR VERIFYING THE CORRECT SETUP OF A BLOOD TREATMENT APPARATUS

(71) Applicant: FRESENIUS MEDICAL CARE DEUTSCHLAND GMBH, Bad Homburg (DE)

(72) Inventors: Klaus Wolf, Arnstein (DE); Bernd Mohr, Zwingenberg (DE); Manuel Hassler, Oberursel (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 498 days.

(21) Appl. No.: 18/255,198

(22) PCT Filed: Dec. 2, 2021

(86) PCT No.: PCT/EP2021/084039
§ 371 (c)(1),
(2) Date: May 31, 2023

(87) PCT Pub. No.: WO2022/117758
PCT Pub. Date: Jun. 9, 2022

(65) Prior Publication Data

US 2024/0016990 A1 Jan. 18, 2024

(30) Foreign Application Priority Data

Dec. 2, 2020 (DE) ..................... 10 2020 131 973.8

(51) Int. Cl.
*A61M 1/28* (2006.01)

(52) U.S. Cl.
CPC .............. *A61M 1/288* (2014.02); *A61M 1/28* (2013.01); *A61M 1/282* (2014.02);
(Continued)

(58) Field of Classification Search
CPC ........ A61M 1/28; A61M 1/282; A61M 1/288; A61M 2205/14; A61M 2205/332;
(Continued)

(56) References Cited

U.S. PATENT DOCUMENTS 5,445,610 A 8/1995 Evert
2019/0376835 A1 * 12/2019 Hassler .................. G01G 17/06
(Continued)

FOREIGN PATENT DOCUMENTS

| | | | |
|---|---|---|---|
| DE | 102016008888 | A1 | 1/2018 |
| WO | 2012143103 | A1 | 10/2012 |
| WO | 2018015020 | A1 | 1/2018 |

*Primary Examiner* — John Kim
(74) *Attorney, Agent, or Firm* — Kilyk & Bowersox, P.L.L.C.

(57) ABSTRACT

The present invention relates to a method for automatically verifying correct setup of a blood treatment apparatus, in particular a gravimetric cycler for peritoneal dialysis having only one scale and a hose system, wherein the hose system comprises at least three line portions for connection to at least one drainage bag, at least one solution bag and a patient, wherein, by means of the scale, a change in weight of the solution bag and/or the drainage bag during a filling process of the hose system is detected and compared to an expected value. Furthermore, the invention relates to a corresponding blood treatment apparatus.

10 Claims, 4 Drawing Sheets

(52) U.S. Cl.
CPC ... *A61M 2205/14* (2013.01); *A61M 2205/332* (2013.01); *A61M 2205/3393* (2013.01); *A61M 2205/502* (2013.01); *A61M 2205/6018* (2013.01)

(58) Field of Classification Search
CPC .... A61M 2205/3393; A61M 2205/502; A61M 2205/6018
See application file for complete search history.

(56) References Cited

U.S. PATENT DOCUMENTS

2020/0179584 A1 6/2020 Wabel
2020/0297909 A1* 9/2020 Suljevic ................ A61M 1/281

* cited by examiner

Valve of solution bag line

Valve of last bag line

Drainage valve a)

b)

c)

Stabilization time

Stabilization time

0

1

2

Examples of "weight deltas" during priming for various bag configurations

| Bag Configuration | Fill level | Calc. Time patient (ms) | Tray weight (g) | Weight delta (g) |
|---|---|---|---|---|
| 2 | 11 | 4000 | 2300 | 45 |
| 2 & 2 | 0 | 3900 | 4300 | 46 |
| 2 & LB | 7 | 3900 | 4400 | 53 |
| 2 & 2 & LB | 6 | 3444 | 6400 | 55 |
| 5 | 40 | 3650 | 5400 | 44 |
| 5 & LB | 25 | 3320 | 7450 | 52 |
| 5 & 5 | 1 | 2950 | 10600 | 50 |
| 5 & 5 & LB | 1 | 2800 | 12600 | 52 |
| 6 | 19 | 3400 | 6500 | 48 |
| 6 & 6 | 4 | 2800 | 12700 | 49 |
| 6 & 6 & LB | 0 | 2700 | 14900 | 56 |

| Bag Configuration | Fill level | Calc. Time patient | Tray weight | Weight delta |
|---|---|---|---|---|
| 2 | 11 | 4000 | 2300 | 45 |
| 2 & 2 | 0 | 3900 | 4300 | 46 |
| 5 | 40 | 3650 | 5400 | 44 |
| 6 | 19 | 3400 | 6500 | 48 |
| 5 & 5 | 1 | 2950 | 10600 | 50 |
| 6 & 6 | 4 | 2800 | 12700 | 49 |

DEVICE AND METHOD FOR VERIFYING THE CORRECT SETUP OF A BLOOD TREATMENT APPARATUS

The present invention relates to a device and method for verifying the correct setup of a blood treatment apparatus, and to a corresponding blood treatment apparatus.

In the context of peritoneal dialysis, in particular automated peritoneal dialysis, blood treatment is usually executed overnight at the corresponding patient's home.

In this method, the blood treatment apparatus or cycler takes over the temperature control of the bags, the emptying and filling of the abdomen, and the therapy control.

For example, the patient sets up the cycler before going to bed (for example by connecting the cycler's hose system to the solution bags and the drainage bag) and connects to the cycler once by means of a connecting hose. Overnight, the automated therapy is performed. Therapy regimen, number and duration of cycles, dialysate turnover and glucose concentration are individually tailored to the patient. In certain cases, the patient may be given a final fill, which may differ from the dialysate concentration to the previous fills. This last fill is usually administered to the patient from a separate bag, referred to as the "last bag," which may remain in the abdomen until the next emptying phase, preferably until midday exchange or the next night.

However, the treatment may also be terminated with a final fill of identical concentration of dialysis solution from the solution bags, which also remains in the patient until the next emptying phase. Furthermore, it may be provided that the treatment can be completed without a final enema.

Since blood treatment is performed at the patient's home, the blood treatment apparatus must be set up by the patient himself without the assistance of medically trained personnel.

In practice, it has been shown that errors in setting up the blood treatment apparatus (e.g. incorrectly connected hose lines, hose lines not correctly connected to the valves, closed clamps and other shut-off elements on the hose lines, kinked or squeezed hose lines, incorrectly opened crushing cones of the solution bags, etc.) occur relatively frequently and jeopardize the success of the treatment.

For example, before starting the actual treatment, the hose system of the blood treatment apparatus must be filled with liquid to remove air from the system. This filling process before the actual start of the treatment is also known as priming.

Priming is usually performed in two steps: First, the hose system between the solution bag(s) and the drainage bag(s) is filled. Then, the line portion leading to the patient is filled.

If priming has not been executed correctly, the subsequent blood treatment cannot be executed correctly, for example, because the necessary volumes cannot flow or there is still air in the system. In most cases, the blood treatment must be terminated prematurely in this case for reasons of patient safety.

The present invention is based on the object of mitigating or even completely eliminating the disadvantages of the prior art. In particular, the present invention is based on the object of improving patient safety during peritoneal dialysis.

This object is achieved by the subject matters of the independent claims. Advantageous further developments of the invention are the subject matter of the dependent claims.

A first aspect of the present invention relates to a method for automatically verifying correct setup of a blood treatment apparatus, preferably a gravimetric cycler for peritoneal dialysis having at least one weighing system and a hose system, wherein the hose system comprises at least three line portions for connection to at least one drainage bag, at least one solution bag and a patient line, wherein, by means of the weighing system, a change in weight of the solution bag and/or the drainage bag during a filling process of the hose system is detected and compared to an expected value.

A wide variety of weight measuring methods, such as scales, load cells, strain gauges, piezo elements, may be used as weighing systems. Preferably, the weighing system has only one scale or load cell. For the sake of simplicity, in the further course of the description, the weighing system will be referred to as a scale, without this implying any limiting effect. By means of the only one scale or load cell, a combined weight of the bag or bags with fresh dialysis fluid and the bag or bags for used dialysis fluid (drain bag) can be detected, for example.

During priming and thus during the execution of a method according to the invention, the patient is preferably not connected to the blood treatment apparatus.

According to the invention, it is thus confirmed whether a change in weight of the solution bag and/or the drainage bag to be expected occurs during a filling process of the hose system.

For example, during a normal filling process, a certain amount (e.g. 50 ml) of liquid flows from the solution bag into the hose system. In this case, the weight of the solution bag from which the liquid flows into the hose system and of the drainage bag detected by means of the scale is expected to decrease by 50 g accordingly.

If the actually measured weight of the solution bag and the drainage bag corresponds to this expected value (for example, initial weight minus 50 g), it can be assumed that the hose system of the blood treatment apparatus is correctly connected to the solution bag, so that the valves open and close properly, no line is pinched or kinked, the solution bag is fluidically released (crushing of a crushing cone), etc.

However, if the blood treatment apparatus is not set up correctly or connected to the hose system so that, for example, the valves do not open and close properly, a line is pinched or kinked, or the solution bag is not fluidically released (uncrushed crushing cone), then either no liquid at all may flow during the attempted filling process (because, for example, the solution bag is still closed) or only partially flow (e.g., up to a squeezed line portion). For example, only a change in weight of the solution bag of minus 20 g instead of minus 50 g is detected. In this case, the expected value of the change in weight is not reached and an incorrect setup of the blood treatment apparatus can be concluded.

The expected value may serve as a minimum value of e.g., a change in weight for correct setup of the blood treatment apparatus. For example, correct setup can be concluded if the detected change in weight reaches at least the value to be expected based on the design of the blood treatment apparatus and its hose system, e.g. 50 g.

Preferably, the filling process of the hose system is performed automatically. Likewise, the verification of the setup of the blood treatment apparatus is preferably performed automatically as part of the filling process. The automatic execution reduces the number of steps to be executed by the patient and avoids sources of error. Preferably, a combined weight and/or a combined change in weight of the solution bag and the drainage bag is determined by means of the scale.

For example, the solution bag(s) (including a last bag, if used) and the drainage bag(s) may be disposed on or metrologically connected to the same scale.

This configuration offers the advantage that it is possible to detect whether the hose system is correctly inserted into or connected to the drainage valve. For example, if the hose system is faultily inserted into the drainage valve so that the drainage valve cannot stop the flow, liquid will flow from the solution bag into the drainage bag during the filling process and will not remain in the hose system. This results in the air present in the hose system not being displaced and the system not being successfully filled with solution.

Since the weight of the solution bag and the drainage bag is detected by means of a common scale, the change in weight is minimal and amounts to approx. 0 g. In this case, the change in weight does not reach the expected value or a tolerance range surrounding it, so that a faulty setup of the blood treatment apparatus can be concluded.

In this case, a user can, for example, be instructed via a corresponding output to check the drainage valve and then start a new filling process.

Preferably, in the context of the present invention, the start of a blood treatment is enabled only after the detection of a correctly executed filling process of a correctly set up blood treatment apparatus.

For example, in the event of a faulty filling process and/or faulty setup of the blood treatment apparatus, a start of a blood treatment is blocked and preferably an output to a user is made, e.g. if the comparison shows a deviation of the change in weight of the solution bag and/or the drainage bag from the expected value or a tolerance range, in particular if the change in weight does not reach the expected value.

If a faulty filling process and/or a faulty setup of the blood treatment apparatus is detected, an output is preferably made to a user in the form of an instruction for action, which prompts him or her to systematically check the setup of the blood treatment apparatus and, for example, to check the crushing cone of the at least one solution bag and/or to check clamps or shut-off elements arranged on the hose system and/or to check whether the line portions of the hose system are correctly connected, in particular whether they are correctly connected to or inserted into the associated valves.

Thus, according to the invention, the user is preferably automatically guided through a problem solving routine. The output may comprise an acoustic signal and/or a visual signal, for example, a blood treatment apparatus according to the invention may be adapted to announce various instructions for action to the user or to display them on a display device, such as a display.

According to the invention, it may be provided that the user must confirm the execution of an instruction for action before a further instruction for action is issued. For example, it may be provided that the user must confirm that he has checked the crushing cone of the solution bag as instructed before the further instruction for action is issued that the user should check the hose clamps. The confirmation may either be made audibly or also by checking off an instruction for action on a display or by actuating another input unit.

If the comparison does not show any deviation of the change in weight of the solution bag and/or the drainage bag from the expected value or if this deviation is within a tolerance range, a start of a blood treatment is preferably enabled.

Alternatively or additionally, it may be provided that a start of a blood treatment is enabled if the detected change in weight exceeds the expected value and preferably remains within a certain tolerance range. In this configuration, the expected value serves as a minimum value at which it is assumed that the hose system is sufficiently filled at the corresponding change in weight. This further ensures that overfilling of the patient line and a risk of contamination due to solution escaping or adhering to the distal end of the patient line is avoided.

When determining the expected value of the change in weight during a filling process, the weight, number and spatial arrangement of the solution bags in relation to each other and/or to the blood treatment apparatus are preferably taken into account in addition to the design of the blood treatment apparatus and the hose system used.

For example, a specified valve opening duration, for example of the valve or solution bag(s), may be set for a filling process for a particular blood treatment apparatus.

Depending on the type of solution bags used (e.g., capacity, weight, etc.) and their arrangement (for example, storage of the bags on top of each other or next to each other, storage of the bags vertically above the blood treatment apparatus or not), a variable amount of liquid flows during the specified valve opening duration. Thus, the expected change in weight during the specified valve opening duration also depends on the type of solution bags used and their arrangement relative to each other and/or to the blood treatment apparatus.

Alternatively or additionally, the number and/or the filling volume of previous incompletely executed filling processes can be taken into account when determining the expected value of the change in weight during a filling process, whereby preferably the expected value decreases as a number of previous incompletely executed filling processes increases.

Preferably, the expected value decreases in such a way that the calculated expected value corresponds to the difference of an expected value for a correct filling process of a correctly set up blood treatment apparatus (for example 50 g) and the cumulative change in weight due to previous faulty filling processes (for example 13 g in filling process 1 and 17 g in filling process 2, i.e. cumulatively 30 g).

For filling process 3 following filling process 2, the expected value of the change in weight is therefore only 20 g (50 g–30 g), since 30 g of liquid has already been fed into the hose system in the previous filling processes and thus only a further 20 g is required until the hose system is sufficiently filled. Alternatively, after a first filling process, the further filling processes can be carried out with constant, reduced filling quantities.

Another aspect of the present invention relates to a blood treatment apparatus, in particular a gravimetric cycler for peritoneal dialysis, having only one scale and a hose system, wherein the blood treatment apparatus is adapted to automatically detect correct setup of the blood treatment apparatus, preferably in the context of a method according to the invention, and wherein the hose system comprises at least three line portions for connection to at least one drainage bag, at least one solution bag and a patient line, wherein the blood treatment apparatus further comprises a detection unit adapted to detect a change in weight of the solution bag and/or the drainage bag by means of the scale during a filling process of the hose system, and an evaluation unit adapted to compare the detected change in weight to an expected value.

Preferably, a blood treatment apparatus according to the invention further comprises a control unit adapted to automatically execute the filling process of the hose system and/or to automatically execute a method according to the invention.

Furthermore, it has proven to be advantageous in practice that the detection unit is adapted to determine a combined weight and/or a combined change in weight of the solution bag and the drainage bag by means of the scale.

The control unit may be adapted to block a start of a blood treatment and to issue a dispensing to a user if the comparison shows a deviation of the change in weight of the solution bag and/or the drainage bag from the expected value or a tolerance range surrounding the expected value, in particular if the change in weight does not reach the expected value or tolerance value (insufficient filling process).

The output to the user may be performed visually or audibly, guiding the user through a sequence of action steps in which the user checks and, if necessary, corrects the setup of the blood treatment apparatus.

For example, the output may prompt the user to check the crushing cone of the at least one solution bag and/or to check clamps or shut-off elements arranged on the hose system and/or to check whether the line portions of the hose system are correctly connected, in particular whether they have been correctly connected to the associated valves. In this way, a source of error in the system setup can be specifically localized and eliminated.

Furthermore, the control unit may be adapted to enable a start of a blood treatment if the comparison does not show any deviation of the change in weight of the solution bag and/or the drainage bag from the expected value or if the change in weight is within a tolerance range above or below the expected value. In other words, the treatment is only released when a properly performed filling process has been detected.

The treatment may also be enabled if the change in weight reaches or exceeds the expected value. The expected value thus serves as a minimum value and reflects the volume that is minimally required to fill the hose system.

The control unit is preferably adapted to take into account the weight, the volume, the number and/or the spatial arrangement of the solution bags relative to each other and/or to the blood treatment apparatus when determining the expected value of the change in weight during a filling process.

Moreover, it has proven to be advantageous in practice that the control unit is adapted to take into account the number and/or the filling volume of previous incompletely executed filling processes when determining the expected value of the change in weight during a filling process, whereby preferably the expected value decreases as a number of previous incompletely executed filling processes increases. Thus, the volume present in the hose system due to previous incompletely executed filling processes is taken into account by the expected value of the respective current filling process.

It is also encompassed by the invention that the method and/or the blood treatment apparatus is designed so as not to or not only to detect a faulty installation of the therapy system (e.g. hose system not inserted correctly, cone of bags not crushed), but also to detect the type of hose system, e.g. a hose system specifically intended for pediatric patients or other patient groups.

In this configuration of the invention, it is provided that a specific treatment mode is set on the blood treatment apparatus (e.g. under apparatus settings or patient limit values) associated with a respective, specific hose system.

For example, it is conceivable to select a pediatric therapy mode, which requires a special hose system for pediatric patients, or to select a "default", i.e. standard therapy mode, which is set for all other patients. This embodiment is based on the concept that various hose systems have different configurations/dimensions and therefore different filling volumes.

Depending on the selected therapy mode (e.g. pediatric or standard), the apparatus expects an appropriate minimum required priming volume to confirm a correctly set system or correctly selected hose system, and would also apply a different priming method to use a higher volume.

For example, if a standard hose set is used instead of a pediatric hose set, the expected priming volume for the pediatric mode cannot be achieved because the standard set can only accommodate the maximum volume (e.g., 50 ml). Hose systems cannot be "overfilled" (filled with more liquid than the maximum possible fill volume) because the hydrophobic membrane of the patient connector does not allow liquid to leave the hose system. The use of a hose system that is not correct, i.e. does not belong to the selected therapy mode, may lead to undesired results (e.g. reduced therapy effectiveness due to a high recirculation volume in relation to the total treatment volume).

As examples, there are mentioned:

Standard hose system/therapy mode: threshold value for priming OK: 40 g, max. priming volume: 50 ml Pediatric hose system/therapy mode: threshold value for priming OK: 60 g, max. priming volume: 70 ml For example, the apparatus is set to the pediatric therapy mode and a standard hose set is accidentally inserted during preparation: The apparatus fills the hose system according to the priming procedure for "pediatric mode" (e.g., opening the valves for a longer time) and expects a minimum change in weight of 60 g. The hose system is completely filled with liquid due to the deviating priming method, resulting in an effective change in weight of 50 g during priming. The apparatus would reject the setup because the required minimum change in weight of the solution bag of 60 g is not achieved.

In the above example, to differentiate between the standard and pediatric hose sets, the threshold value for the pediatric hose system (60 g) must be greater than the maximum possible priming volume for the standard set (50 g).

The aforementioned embodiment of the invention thus relates to the detection of a faulty hose system based on the knowledge that the filling, i.e. priming, volume does not correspond to the expected filling volume. This detection assumes that the different hose systems have different maximum filling volumes.

BRIEF DESCRIPTION OF THE DRAWINGS

Further advantages, features and effects of the present invention will be apparent from the following detailed description of preferred embodiments of the invention with reference to the figures, in which identical reference signs denote identical or similar components or steps. They show.

DETAILED DESCRIPTION OF THE INVENTION

Figure 1:
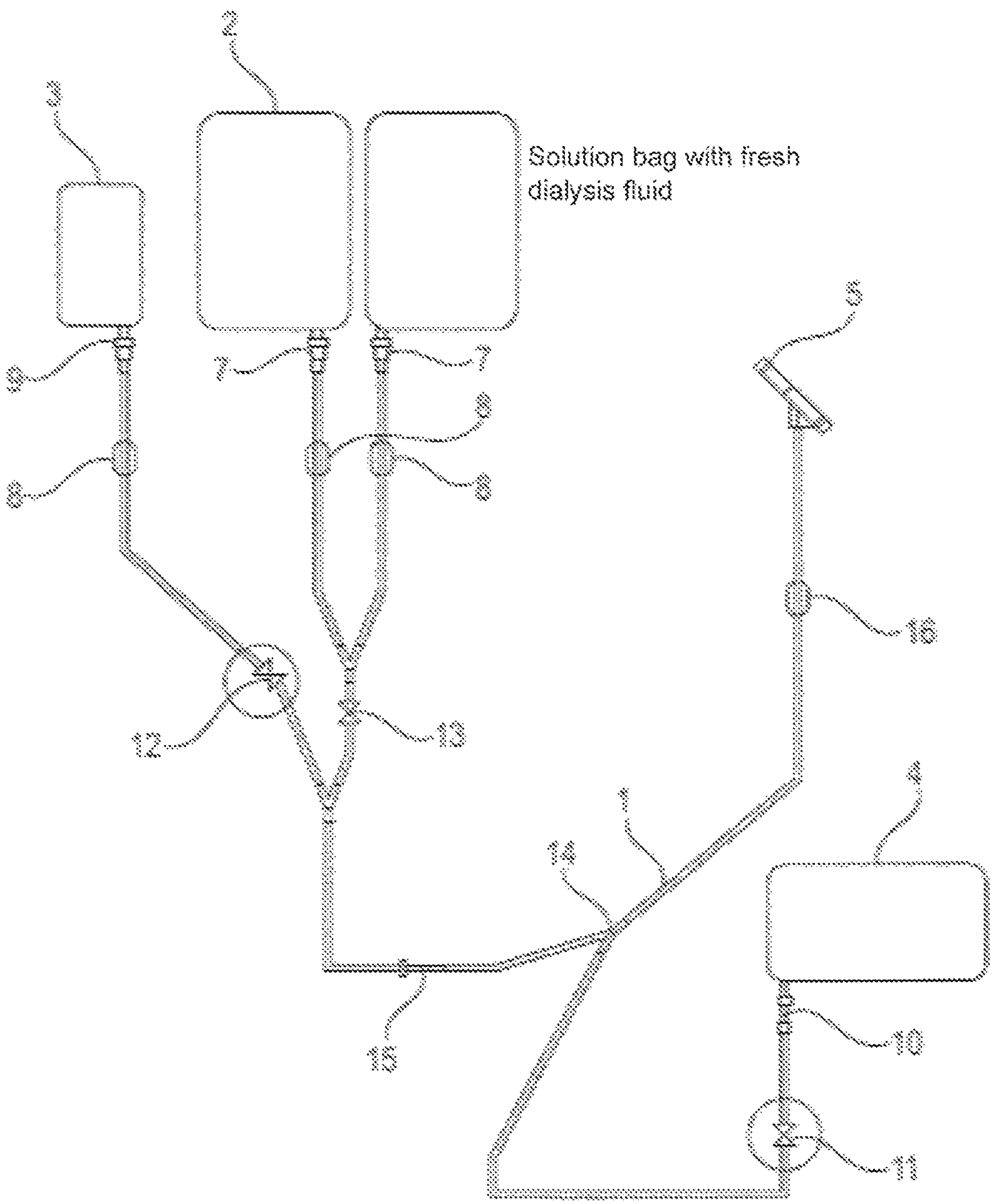
FIG. 1 illustrates the structure of a blood treatment apparatus according to the invention.

As shown in FIG. 1, a gravimetric peritoneal dialysis device comprises a hose system 1 fluidically connecting two solution bags 2 with fresh dialysis fluid, a last bag 3, a drainage bag 4, and a patient access port 5.

The solution bags 2 are each equipped with a crushing cone 7. The last bag 3 is equipped with a crushing cone 9. A clamp 8 is fluidically connected downstream of each of the crushing cones 7 and 9. The drainage bag 4 may be equipped with a crushing cone 10, upstream of which a valve 11 is fluidically connected.

A valve 12 or 13, in particular a valve of a peritoneal dialysis apparatus, is arranged in the line from the last bag 3 and the line from the solution bags 2. AY-shaped connecting piece 14 is arranged between the solution bags 2 and the last bag 3 and the patient connector 5. A connection point 15 is provided between the solution bags 2 and the last bag 3 and the Y-shaped connection piece 14, which may also be equipped with a crushing cone so that the emptied solution bag set can be separated from the drainage set and reused as a drainage bag in a subsequent treatment. A clamp 16 is arranged between the connector 14 and the patient access port 5. However, this clamp 16 is not essential for executing a method according to the invention and may be omitted.

Figures 2, 3:
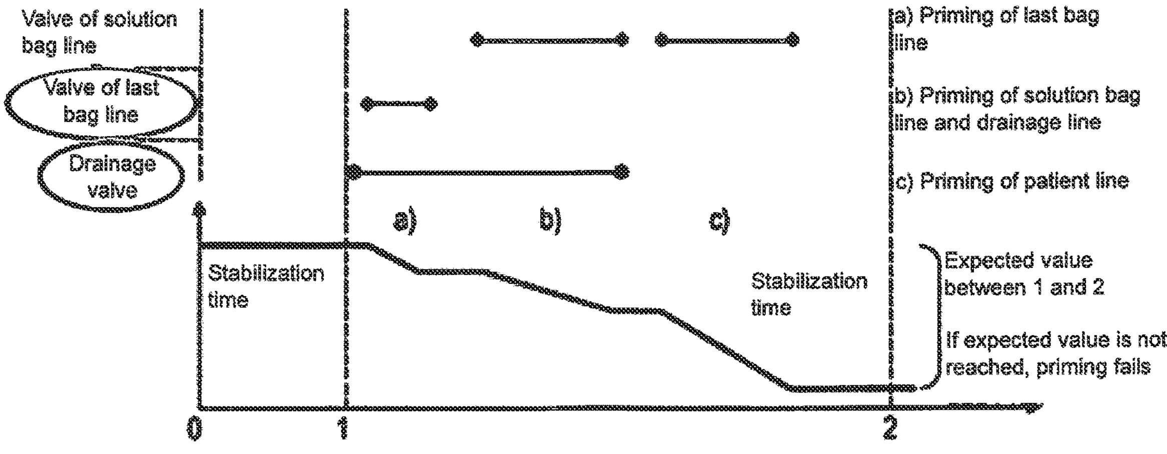
FIG. 2 is an overview of a method according to the invention.
FIG. 3 is an overview of a further method according to the invention.

FIG. 2 shows the valve opening times and the correspondingly measured changes in the combined weight of the solution bags and the drainage bag. The Y-axis indicates the measured weight, the X-axis indicates time. In this representation, it is assumed that the crushing cones of all bags are correctly opened and the entire system is correctly set up.

The priming process starts at time 0, at which a user confirms the start of priming. The system waits a short time (e.g. 8 s) until time 1 to give the system time to stabilize.

As soon as the detected weight is stable, the weight at time 1 is stored as the initial weight. If the treatment prescription stipulates a final filling from the last bag, the valve 12 of the last bag line and the drainage valve 11 are then opened. This phase, in which the last bag line is filled, is marked as phase a) in FIG. 2. The detected weight decreases gradually (linearly) due to the liquid flowing into the last bag line and reaches a plateau at the end of phase a), when no further liquid flows, since the last bag line is filled.

After phase a) is completed, the valve 12 of the last bag line is closed and the valve 13 of the solution bag line is opened. This fills the solution bag line and the drainage bag line. This phase is designated as phase b) in FIG. 2. The detected weight decreases linearly in phase b) as liquid flows from the solution bags 2 into the lines. At the end of phase b), the weight reaches a plateau since no more liquid flows since the valves are closed. In this case, the valve 11 is closed immediately or simultaneously with the valve 12 to prevent the drainage line from running empty.

The patient line is then filled after a short stabilization time or valve changeover time in phase c). For this purpose, the drainage valve 11 is closed and the valve 13 of the solution bag line, which was closed during the stabilization or changeover time, is opened. The detected weight decreases linearly in phase c) since further liquid flows from the solution bags 2 into the patient line.

The opening duration of the valve 13 of the solution bag line in phase c) depends on the number, type, weight and arrangement of the solution bags used. Depending on the solution bags used, the flow rate through the solution bag line varies, so that different valve opening durations are required to achieve a defined volume in the line. By adjusting the valve opening duration, overfilling of the patient line and/or possible contamination can be prevented. Another advantageous effect of an exact filling process is that when filling the hose system, only as much dialysis solution as necessary is consumed to flush the complete hose system and thus the remaining solution is available for efficient treatment.

After the end of phase c), a further stabilization time is waited for. As soon as the detected weight has stabilized, it is stored as the final weight. From the difference between the initial weight and the final weight, the detected change in weight during the filling process may be determined.

If this change in weight reaches or exceeds an expected value, it can be concluded that the filling process has been executed successfully, as a sufficient amount of liquid has flowed into the hose system and also remains there. This state can only be achieved if the complete system has been set up correctly. In this case, the execution of a blood treatment can be enabled.

If the change in weight does not reach the expected value, a corresponding output is issued to the user with a request to check the setup of the blood treatment apparatus and then to repeat the filling process if necessary. In the repeated filling processes, the expected value is set to be lower than in the previous filling processes to account for a partially filled hose system.

If the blood treatment apparatus is set up correctly, the expected change in weight is preferably between about 45 g and about 55 g.

If the hose system is not or incorrectly inserted into the valve 12 and/or the valve 13, liquid already flows from the bags 3 and 2 into the hose system before the actual filling process. Thus, during the filling process, no further liquid flows and the change in weight is about 0 g.

According to one embodiment, a patient hose clamp 16 is present in the blood treatment apparatus and the user has the option of manually readjusting the filling process. For this purpose, a control panel may be provided on the blood treatment apparatus, via which the patient can refill the hose system in incremental filling quantities. However, the ability to manually adjust the filling process, preferably via the control panel, is independent of the presence of the patient hose clamp 16. In a particular embodiment, the patient clamp may be omitted. If the hose system is incorrectly inserted into the valve 11, liquid from the bags 3 and 2 will flow unimpeded through the hose system to the drainage bag 4. Since the scale detects a combined weight of the bags 2, 3 and 4, the detected change in weight is about 0 g even in this case.

In this case, the user may be instructed to check whether the hose system is inserted incorrectly into the valve 11, to correct this accordingly and then to start another filling process. In this way, it can be determined why the missing change in weight was detected.

Even if the crushing cones of the bags 2 and 3 or the clamps 8 have not been opened, no change in weight may be detected. In this case, the user may be instructed to check whether the crushing cones and clamps are open, to correct this accordingly if necessary and then to start another filling process.

The user is thus offered solution approaches when an incorrect setup of the blood treatment apparatus is detected, e.g. by checking the crushing cones and clamps and/or by checking whether the hoses are correctly inserted into the valves.

To further increase patient safety, an additional step may be added at the end of the method shown in FIG. 2, as shown in FIG. 3. A combination of a drainage line not inserted into the drainage valve and closed clamps on the drainage line may not be detected as a faulty setup of the blood treatment apparatus by the method shown in FIG. 2, since the liquid remains in the hose system due to the closed clamps (even though the valve 11 cannot shut off the drainage line) and thus a correct change in weight is detected.

In order to detect this error condition, as shown in FIG. 3, after the second stabilization time has elapsed, the drainage valve 11 is opened, causing the detected weight to increase linearly as liquid flows into the drainage bag 4. In the case of a closed clamp on the drainage line, the weight would not increase because no liquid can flow.

The hose system or patient line is then filled again by opening the valves 12 and/or 13, preferably valve 13 of the solution bag line(s), and clamps 8. The detected weight thereby decreases linearly as liquid flows from the solution bags 2 and/or from the solution bag 3 into the hose system.

The valve opening duration of the valves in phases a) and b) is preferably set depending on the type, number, weight and spatial arrangement of the solution bags used. The valve opening duration in phase a) may be e.g. 1000 ms, in phase b) it may be 2000 ms.

Figures 4, 5:
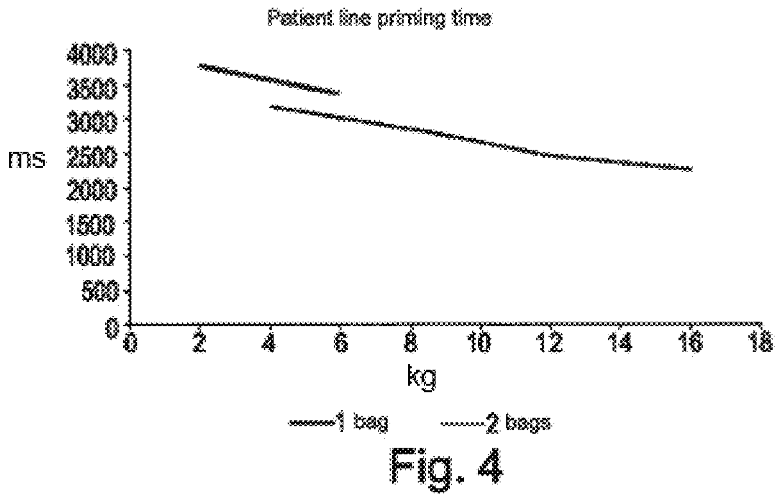
FIG. 4 is a chart showing the relationship between the type of solution bags used and the valve opening times required for a filling process.
FIG. 5 is a table with characteristic values of a method according to the invention.

In FIG. 4, for example, the weight of a solution bag used is plotted in kg on the X axis. The Y axis indicates the required valve opening duration in ms.

The filling speed of the hose system and, in particular, of the patient line is related to the total volume of the solution bags used as well as to the number of bags.

If, for example, several bags are stored on top of each other, the pressure in the bags increases and a shorter valve opening duration is required to feed a defined volume from the bags into the hose system. In FIG. 4, for example, the bottom line shows the case of two bags stored on top of each other.

If only one bag is used, the filling speed increases as the volume of the bag increases. In other words, the required valve opening duration decreases as the volume of the bag increases. In FIG. 5, for example, the top line shows the case of a single bag inserted.

The type, number, weight and spatial arrangement of the solution bags used are also taken into account when determining an expected value of the change in weight during a filling process. This is shown in FIG. 5, where the column "weight delta" shows the respective expected change in weight for various bag configurations.

As shown in the table of FIG. 5 in the first column, for an arrangement of 2 bags (see column "Bag configuration"), with a detected initial weight of 2300 g ("Tray weight"), a valve opening duration of 4000 msec ("Calc.Time patient") can be considered sufficient for filling the hose system, in particular for filling the patient line. The expected change in weight for a correct filling process of such a blood treatment apparatus is 45 g (see "weight delta").

If two bags are used (second row in column 1 "Bag configuration"), each weighing 2150 g and stored, for example, on top of each other, only an opening duration of 3900 ms is required and the expected change in weight is 46 g.

If a last bag is also used (third row in column 1 "Bag configuration"), the total weight of the bags is 4400 g and an opening duration of 3900 ms is required and the expected change in weight is 53 g.

Since a slight deviation of the detected change in weight from the expected value may occur even when a blood treatment apparatus is set up correctly, a correctly set up blood treatment apparatus as well as a correctly executed filling process can be concluded if the detected change in weight falls within a tolerance range.

In the table in FIG. 5, the "Filling level" column indicates the distance between the patient connector and the filling level of the solution in the hose. Here, a low value indicates a high filling level of the solution in the hose, while a higher value reflects a low filling level. A distance of between 15 cm and 20 cm is preferred as a tolerance to avoid wetting of the hydrophobic membrane.

Figure 6:
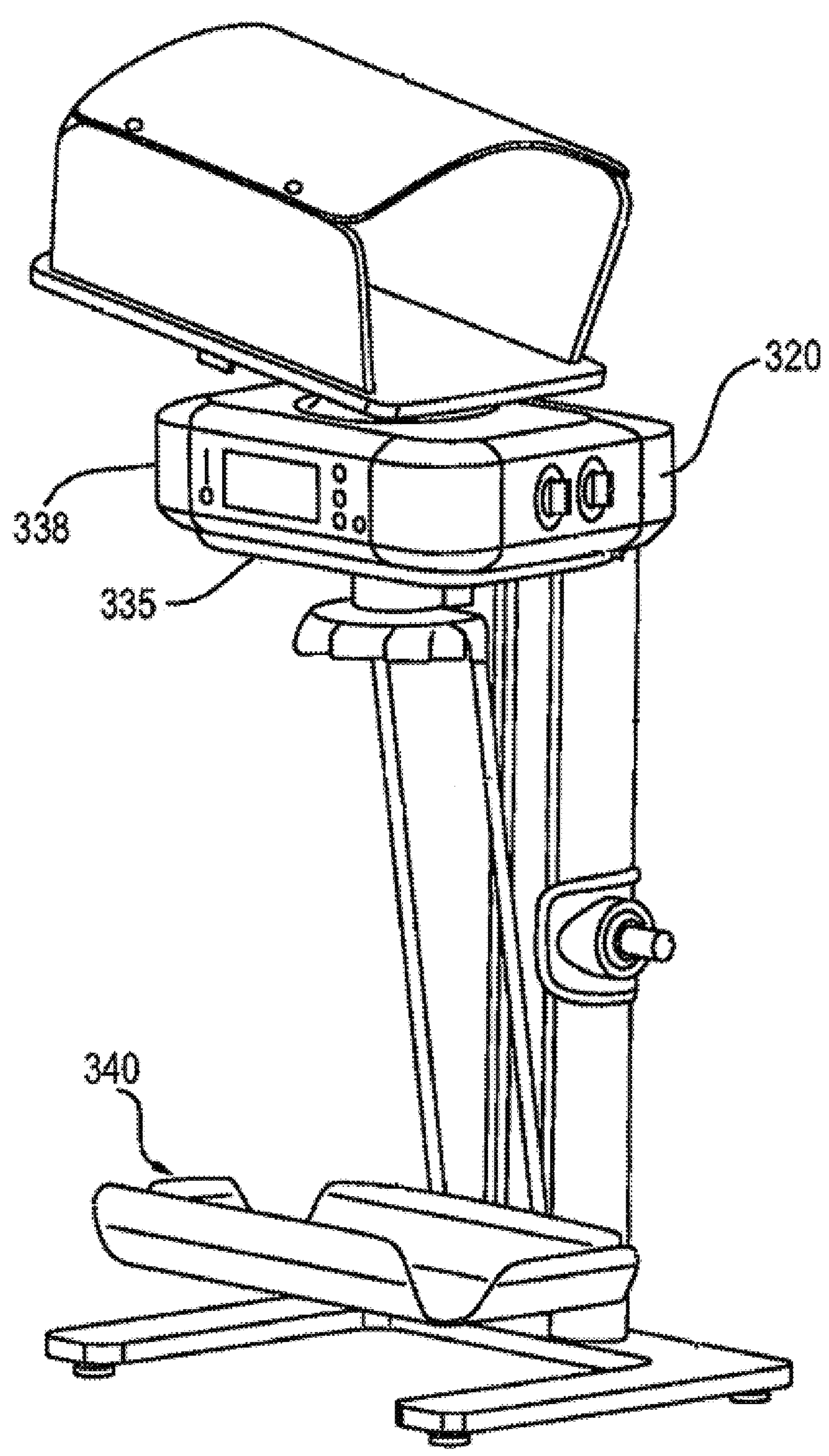
FIG. 6 is a perspective view of a blood treatment apparatus according to the invention.

FIG. 6 illustrates a blood treatment apparatus having a scale 340, a detection unit 320, an evaluation unit 338, and a control unit 335.

The invention claimed is:

1. A method for automatically verifying correct setup of a blood treatment apparatus, the blood treatment apparatus comprising only one scale, a hose system, and a control unit, wherein the hose system comprises at least three line portions for connection to at least one drainage bag, at least one solution bag and a patient line, the method comprising:

detecting a combined weight and/or a combined change in weight of the solution bag and the drainage bag measured by the scale during a filling process of the hose system;

comparing the combined weight and/or the combined change in weight to an expected value; and blocking a start of a blood treatment and generating an output by the control unit when a deviation of the combined weight and/or the combined change in weight of the solution bag and the drainage bag from the expected value or a tolerance range of the expected value is determined, wherein the output comprises instructions for a problem solving routine, the output being in a form of an acoustic signal and/or a visual signal prompting a user to check a crushing cone of the at least one solution bag and/or to check clamps or shut-off elements arranged on the hose system and/or to check whether the line portions of the hose system are correctly connected.

2. The method according to claim 1, wherein the filling process of the hose system is performed automatically.

3. The method according to claim 1, further comprising enabling a start of the blood treatment when no deviation of the combined weight and/or the combined change in weight of the solution bag and the drainage bag from the expected value is determined or when the solution bag and/or the drainage bag is within a tolerance range of the expected value.

4. The method according to claim 1, wherein a weight, a type of hose system, a number and spatial arrangement of the solution bags relative to each other and/or to the blood treatment apparatus are taken into account when determining the expected value of the combined weight and/or the combined change in weight during the filling process.

5. The method according to claim 1, wherein a number and/or a filling volume of previous incompletely executed filling processes is taken into account when determining the expected value of the combined weight and/or the combined change in weight during the filling process.

6. A blood treatment apparatus comprising only one scale, a hose system, a detection unit, an evaluation unit, and a control unit, wherein the blood treatment apparatus is configured to automatically detect correct setup of the blood treatment apparatus by the method according to claim 1, wherein the hose system comprises at least three line portions for connection to at least one drainage bag, at least one solution bag and a patient line, wherein the detection unit is configured to detect a combined weight and/or a combined change in weight of the solution bag and the drainage bag measured by the scale during a filling process of the hose system, the evaluation unit is configured to compare the detected combined weight and/or combined change in weight to an expected value, and when the comparison shows a deviation of the combined weight and/or the combined change in weight of the solution bag and the drainage bag from the expected value or a tolerance range of the expected value, the control unit is configured to block a start of a blood treatment and generate an output, the output comprising instructions for a problem solving routine comprising a prompt for a user to check a crushing cone of the at least one solution bag and/or to check clamps or shut-off elements arranged on the hose system and/or to check whether the line portions of the hose system are correctly connected.

7. The blood treatment apparatus according to claim 6, wherein the control unit is configured to automatically execute the filling process of the hose system and/or the method for automatically verifying correct setup of the blood treatment apparatus.

8. The blood treatment apparatus according to claim 6, wherein the control unit is configured to enable a start of a blood treatment when the comparison does not show any deviation of the combined weight and/or the combined change in weight of the solution bag and the drainage bag from the expected value or when the change in weight is within a tolerance range above and/or below the expected value.

9. The blood treatment apparatus according to claim 6, wherein the control unit is configured to take into account a weight, a number and/or a spatial arrangement of the solution bags relative to each other and/or to the blood treatment apparatus when determining the expected value of the combined weight and/or the combined change in weight during the filling process.

10. The blood treatment apparatus according to claim 6, wherein the control unit is configured to take into account a number and/or a filling volume of previous incompletely executed filling processes when determining the expected value of the change in weight during the filling process.

* * * * *